United States Patent
Esswein et al.

(10) Patent No.: US 6,444,832 B1
(45) Date of Patent: Sep. 3, 2002

(54) AMINO ALCOHOL DERIVATIVES, METHOD OF PRODUCING SAID DERIVATIVES AND MEDICAMENTS CONTAINING THEM

(76) Inventors: Angelika Esswein, Birkenweg 4, D-64572, Büttelborn (DE); Lothar Kling, Neckarpromenade 34, D-68167, Mannheim (DE); Ulrike Leser, Elisabethstrasse 26, D-80796, München (DE); Walter-Gunar Friebe, Sophienstrasse 8, D-68165, Mannheim (DE)

( * ) Notice: Subject to any disclaimer, the term of this patent is extended or adjusted under 35 U.S.C. 154(b) by 0 days.

(21) Appl. No.: 09/407,981

(22) Filed: Sep. 29, 1999

Related U.S. Application Data

(63) Continuation of application No. 09/069,000, filed as application No. PCT/EP98/05212 on Nov. 26, 1996.

(30) Foreign Application Priority Data

Nov. 30, 1995 (DE) .......................................... 195 44 635

(51) Int. Cl.$^7$ ............................................ C07C 231/00
(52) U.S. Cl. .............................. 554/68; 554/66; 554/69; 514/625; 514/627
(58) Field of Search ................................ 54/68, 69, 64; 514/625, 627

(56) References Cited

FOREIGN PATENT DOCUMENTS

WO 94/12466 * 6/1994 ......... C07C/233/00

* cited by examiner

Primary Examiner—Deborah D. Carr

(57) ABSTRACT

Compounds of formula I

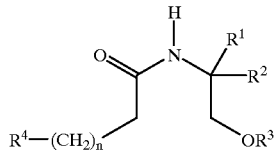

(I)

in which
 $R^1$ denotes hydrogen or methyl
 $R^2$ denotes lower straight-chained or branched alkyl with 1 to 10 carbon atoms
 $R^3$ denotes hydrogen or lower alkyl
 n denotes 0–12
 $R^4$ denotes alkyl, alkenyl or alkinyl with 6 to 24 carbon atoms,
processes for the production thereof as well as pharmaceutical agents containing these compounds for the treatment of osteoporosis.

8 Claims, No Drawings

AMINO ALCOHOL DERIVATIVES, METHOD OF PRODUCING SAID DERIVATIVES AND MEDICAMENTS CONTAINING THEM

This is a continuation application of U.S. patent application Ser. No. 09/069,000, filed on Dec. 14, 1998, which is a 371 of PCT/EP96/05212 filed Nov. 26, 1996 the disclosure of which is hereby incorporated by reference.

The present invention concerns new amino alcohol derivatives, processes for their production as well as pharmaceutical agents which contain these substances.

In healthy persons the anabolic and catabolic processes in the bone are almost in equilibrium i.e. the activity of the osteoblasts and osteoclasts is balanced. However, if this equilibrium is disturbed in favour of the osteoclasts and/or in favour of the osteoblasts the bone mass is reduced and there is a negative change in bone structure and function.

Inhibitors of bone resorption such as oestrogens, calcitonin and bisphosphonates have previously been used to treat disturbances of bone metabolism. However, the use of these substances is limited and also does not exhibit the desired effect in all cases. Compounds which have a stimulating effect on the formation of bone and in addition contribute to increasing an already reduced bone mass are therefore extremely important for the treatment of disturbances of bone metabolism. Substances with an osteoanabolic action for the therapy of osteoporosis were described in the European Patent Applications EP-A-625522 and EP-A-524023.

Surprisingly it was now found that amino alcohol derivatives of the present invention have a stimulating effect on the formation of bone and are therefore suitable for the broad treatment of disturbances of bone metabolism. They can be used particularly well for cases in which the formation of bone is disturbed i.e. they are suitable for the treatment of osteopenic diseases of the skeletal system such as e.g. osteoporosis including osteogenesis imperfecta but also to support bone regeneration and osteoinduction such as e.g. in orthopaedic and orthodontic indications, in the healing of fractures, osteosyntheses, pseudoarthroses and the settling of bone implants.

Based on these properties they can also be used in the prevention of osteoporosis.

As a result of their influence on bone metabolism they additionally form a basis for the treatment of rheumatoid arthritis, osteoarthritis and degenerative arthrosis.

The present invention concerns new compounds of the general formula (I)

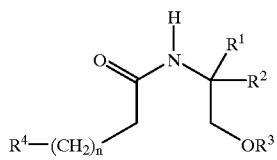

(I)

in which
R$^1$=hydrogen or methyl
R$^2$=lower straight-chained or branched alkyl with 1 to 10 carbon atoms
R$^3$=hydrogen or lower alkyl
n=0–12
R$^4$=alkyl, alkenyl or alkinyl with 6 to 24 carbon atoms, wherein in the case that
R$^4$ denotes alkyl, —(CH$_2$)$_n$—R$^4$ may not be an unbranched alkyl chain with 8, 10, 12, 14 or 16 carbon atoms
and in the case that R$^2$ denotes methyl or isobutyl, —(CH$_2$)$_n$—R$^4$ may not be (all-cis-4,7,10,13)-octadecatetraene as well as pharmacologically acceptable salts and optical isomers thereof.

In EP-A-208961 amino alcohol derivatives of formula (I) are described in which R$^1$ denotes hydrogen or methyl, R$^3$ denotes hydrogen, R$^2$ denotes methyl or isopropyl and in which —(CH$_2$)$_n$—R$^4$ denotes an unbranched alkyl chain with 14 carbon atoms. In J. Med. Chem. 35, 2939–51 (1995) amino alcohol derivatives of formula (I) are described in which R$^1$, R$^3$ denote hydrogen, R$^2$ denotes methyl or isobutyl and in which —(CH$_2$)$_n$—R$^4$ denotes an unbranched alkyl chain with 14 carbon atoms. A compound of formula (I) is described in Biochem. J. 288, 167–73 (1992) in which R$^1$, R$^3$ denote hydrogen, R$^2$ denotes isobutyl and in which —(CH$_2$)$_n$—R$^4$ denotes an unbranched alkyl chain with 10 carbon atoms. In J. Lipid Res. 13 (1), 86–91 (1972) and in DE-A-3418525 compounds of formula (I) are described in which R$^1$, R$^3$ denote hydrogen, R$^2$ denotes ethyl and in which —(CH$_2$)$_n$—R$^4$ denotes an unbranched alkyl chain with 8, 10, 12, 14 and 16 carbon atoms. All compounds are described as intermediate products without information on a possible use as pharmaceutical agents. Compounds of formula (I) in which R$^1$, R$^3$ are hydrogen, R$^2$ is methyl or isobutyl and in which —(CH$_2$)$_n$—R$^4$ is (all-cis-4,7,10,13)-octadecatetraene have been described in Life Sci. 56 (23/24), 2041–8 (1995) as cannabinoid receptor ligands.

Therefore pharmaceutical agents are also a subject matter of the invention which contain compounds of formula I

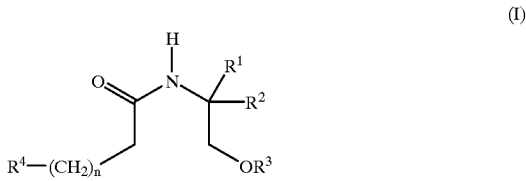

(I)

in which
R$^1$=hydrogen or methyl
R$^2$=lower straight-chained or branched alkyl with 1 to 10 carbon atoms
R$^3$=hydrogen or lower alkyl
n=0–12
R$^4$=alkyl, alkenyl or alkinyl with 6 to 24 carbon atoms
as well as pharmacologically acceptable salts and optical isomers thereof.

Lower alkyl is intended in all cases to represent a straight-chained or branched C$_1$–C$_6$ alkyl group such as e.g. methyl, ethyl, propyl, isopropyl, butyl, isobutyl, pentyl or hexyl in particular methyl, ethyl, propyl and butyl.

Alkyl is intended in all cases to represent a straight-chained or branched C$_6$–C$_{18}$ alkyl group such as e.g. hexyl, isohexyl, 2,2-dimethylhexyl, 5-methylhexyl, heptyl, isoheptyl, 6-methylheptyl, octyl, isooctyl, nonyl, isononyl, decyl, isodecyl, undecyl, isoundecyl, dodecyl, isododecyl, tridecyl, isotridecyl, tetradecyl, isotetradecyl, pentadecyl, isopentadecyl, hexadecyl, heptadecyl, isoheptadecyl or octadecyl in particular heptyl, decyl and dodecyl.

Alkenyl denotes in all cases a monounsaturated or polyunsaturated, optionally substituted, residue with 6–20 carbon atoms such as e.g. $\Delta^1$-hexenyl, $\Delta^1$-octenyl, $\Delta^9$-nonenyl, $\Delta^1$-decenyl, $\Delta^{10}$-decenyl, $\Delta^{1,4}$-decadienyl, $\Delta^{1,4,7}$-decatrienyl, $\Delta^{1,4,7,10}$-hexadecatetraenyl, $\Delta^1$-dodecenyl, $\Delta^5$-dodecenyl, $\Delta^{1,4}$-undecadienyl, $\Delta^{14}$- tetradecenyl, in particular $\Delta^1$-decenyl, $\Delta^{1,4}$-decadienyl, $\Delta^{1,4,7}$-decatrienyl in which the double bonds can be cis or trans and in the case of polyunsaturated compounds all combinations are possible.

Alkinyl denotes in all cases a monounsaturated or polyunsaturated optionally substituted, residue with 6–20 carbon atoms such as e.g. $\Delta^1$-decinyl, $\Delta^1$-noninyl, $\Delta^{1,3}$-tetradecadiinyl, $\Delta^{1,3}$-hexadecadiinyl, $\Delta^{1,3}$-octadecadiinyl, in particular $\Delta^1$-decinyl.

Compounds of the general formula (I) contain at least one asymmetric carbon atom and therefore optically active compounds of the general formula (I) are also a subject matter of the present application.

Compounds of the general formula (I) are obtained by known processes for the formation of carboxylic acid amides from the amino alcohols of the general formula (II),

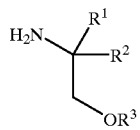

(II)

in which $R^1$, $R^2$ and $R^3$ have the above-mentioned meanings and carboxylic acid derivatives of the general formula (III),

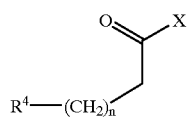

(III)

in which $R^4$ and n have the meanings stated above and X can be a hydroxy or an activation group whereby if X denotes hydroxy, the carboxyl group can be activated by the carbodiimide process and if X denotes an activating group, mixed anhydrides come into consideration and especially with lower alkyl esters of carbonic acid such as ethyl or isobutyl esters or active esters in particular p-nitrophenyl, 2,4,5-trichlorophenyl, N-hydroxysuccinimide or 1-hydroxybenzotriazole esters, or by condensation with nitrites of the general formula (IV)

in which $R^4$ and n have the meanings stated above (cf. Liebigs Ann. Chem. 986–96 (1979)).

Compounds of the general formula (II) are produced by known processes preferably by the reduction of amino acids or they are commercially available.

Compounds of the general formula (III) are produced by known processes from compounds of the general formula (V)

in which $R^4$ and n have the meanings stated above.

Compounds of the general formula (IV) are produced by known processes for the synthesis of nitriles or they are commercially available.

Compounds of the general formula (V) are produced by known processes for chain elongation or synthesis of carboxylic acids or they are commercially available.

Pure enantiomers of the compounds of formula (I) can be obtained by using optically active amino alcohols which can be produced by known processes e.g. by classical racemate resolution via salt formation with optically active acids or by reduction of optically active amino acids.

Compounds of the formula (I) can be administered orally, enterally, parenterally, topically, nasally, pulmonary or rectally in a liquid, solid or aerosol form in all usual non-toxic pharmaceutically acceptable carrier materials, adjuvants and additives. The compounds of formula (I) can be also applied locally on/or in the bones (possibly in a surgical operation). In this connection the term parenterally encompasses subcutaneous, intravenous and intramuscular administration or infusions. Oral forms of application can be for example tablets, capsules, coated tablets, syrups, solutions, suspensions, emulsions, elixirs etc. which can contain one or several additives from the following groups such as e.g. flavourings, sweeteners, dyes and preservatives. Oral forms of administration contain the active component together with non-toxic pharmaceutically acceptable carrier materials which are suitable for the production of tablets, capsules, coated tablets etc. such as e.g. calcium carbonate, sodium carbonate, lactose, calcium phosphate or sodium phosphate; starch, mannitol, methylcellulose, talcum, highly dispersed silicic acids, higher molecular fatty acids (such as stearic acid), peanut oil, olive oil, paraffin, miglyol, gelatin, agar-agar, magnesium stearate, bee wax, cetyl alcohol, lecithin, glycerol, animal and vegetable fats, solid high molecular polymers (such as polyethylene glycols). Tablets, capsules, coated tablets etc. can be provided with an appropriate coating such as e.g. glyceryl monostearate or glyceryl distearate to prevent undesired side-effects in the stomach or to increase the duration of action by a delayed absorption in the gastro-intestinal tract. As an injection medium sterile injectable aqueous or oily solutions or suspensions are preferably used which contain the usual additives such as stabilizers and solubilizers. Such additives can for example be water, isotonic saline solution, 1,3-butanediol, fatty acids (such as oleic acid), monoglycerides and diglycerides or miglyol. All suitable non-irritating additives can be used for the rectal application which are solid at normal temperatures and liquid at rectal temperature such as e.g. cacao butter and polyethylene glycol. For aerosol application the pharmaceutically common carrier media are used. Creams, tinctures, gels, solutions or suspensions etc. containing pharmaceutically common additives are used for external applications.

An application directly on/or in the bones (possibly in a surgical operation) can either be achieved in a solution or suspension or bound to a carrier advantageously by infusion or injection (preferably locally) Carrier-bound compounds of formula (I) can for example be administered as gels, pastes or as a coating on implants.

Biocompatible and preferably biodegradable materials are used as a carrier. The materials preferably themselves additionally induce wound healing or osteogenesis.

For the local application it is preferable to embed the compounds of formula (I) in polymeric gels or films, to immobilize them in this manner and to apply this preparation directly to the site on the bones to be treated. Such polymeric base gels or films are composed for example of glycerol, methylcellulose, hyaluronic acid, polyethylene oxides and/or polyoxamers. Collagen, gelatine and alginate are also suitable and described for example in WO 93/00050 and WO 93/20859. Further polymers are polylactic acid (PLA) and copolymers of lactic acid and glycollic acid (PLPG) (Hollinger et al., J. Biodem. Mater. Res. 17 71–82 (1983)) as well as the bone derivative "demineralized bone matrix" (DBM) (Guterman et al. Kollagen Rel. Res. 8 419–4319 (1988). Polymers which are used for example to adsorb TGFB are also suitable and described in EP-A-0 616

814 and in EP-A-0 567 391 and synthetic bone matrices according to WO 91/18558.

Other suitable carriers for compounds of formula (I) are materials which are usually used in the implantation of bone substitutes or of other therapeutically active substances. Such carriers are based for example also on calcium sulfate, tricalcium phosphate, hydroxyapatite and polyanhydrides. Apart from these biodegradable carriers, carriers are also suitable which are not biodegradable but biocompatible. Such carriers are for example sintered hydroxylapatite, bioglass, aluminates or other ceramic materials (e.g. calcium aluminate phosphate). These materials are preferably used in combination with the biodegradable materials such as in particular polylactic acid, hydroxylapatite, collagen or tri-calcium phosphate. Further non-degradable polymers are described for example in the U.S. Pat. No. 4,164,560.

It is particularly preferable to use a carrier which continuously releases the compounds of formula (I) at the site of action. Slow release pellets from Innovative Research of America, Toledo, Ohio, USA are for example particularly suitable for this. Pellets are particularly preferably used which release the compounds of formula (I) over several days preferably up to 100 days at a daily dose of 1–10 mg/kg per day.

The dosage can depend on various factors such as the mode of administration, species, age and/or individual state. The daily dose that has to be administered of the active substance is 0.01 mg to approximately 100 mg/kg body weight, preferably 0.1 to 10 mg/kg body weight and can be administered singly or divided into several doses.

Apart from the compounds mentioned in the examples and compounds derived by combining all meanings of the substituents stated in the claims the following amino alcohol derivatives are preferred within the sense of the present invention:

Preferred Compounds (PC)
(1) [1-(Hydroxymethyl)-ethyl]-octanamide
(2) [1-(Hydroxymethyl)-propyl]-octanamide
(3) [1-(Hydroxymethyl)-pentyl]-octanamide
(4) [1-(Hydroxymethyl)-ethyl]-7-methyloctanamide
(5) [1-(Hydroxymethyl)-butyl]-7-methyloctanamide
(6) [1-(Hydroxymethyl)-propyl]-7,7-dimethyloctanamide
(7) [1-(Hydroxymethyl)-pentyl]-7,7-dimethyloctanamide
(8) [1-(Hydroxymethyl)-ethyl]-nonanamide
(9) [1-(Hydroxymethyl)-butyl]-nonanamide
(10) [1-(Hydroxymethyl)-ethyl]-4-methylnonanamide
(11) [1-(Hydroxymethyl)-propyl]-8-methylnonanamide
(12) [1-(Hydroxymethyl)-ethyl]-decanamide
(13) [1-(Hydroxymethyl)-butyl]-decanamide
(14) [1-(Hydroxymethyl)-propyl]-undecanamide
(15) [1-(Hydroxymethyl)-pentyl]-undecanamide
(16) [1-(Hydroxymethyl)-ethyl]-10-methylundecanamide
(17) [1-(Hydroxymethyl)-butyl]-10-methylundecanamide
(18) [1-(Hydroxymethyl)-propyl]-dodecanamide
(19) [1-(Hydroxymethyl)-pentyl]-dodecanamide
(20) [1-(Hydroxymethyl)-pentyl]-11-methyldodecanamide
(21) [1-(Hydroxymethyl)-butyl]-11-methyldodecanamide
(22) [1-(Hydroxymethyl)-pentyl]-tridecanamide
(23) [1-(Hydroxymethyl)-pentyl]-12-methyltridecanamide
(24) [1-(Hydroxymethyl)-ethyl]-tetradecanamide
(25) [1-(Hydroxymethyl)-pentyl]-tetradecanamide
(26) [1-(Hydroxymethyl)-butyl]-13-methyltetradecanamide
(27) [1-(Hydroxymethyl)-pentyl]-13-methyltetradecanamide
(28) [1-(Hydroxymethyl)-ethyl]-pentadecanamide
(29) [1-(Hydroxymethyl)-propyl]-pentadecanamide
(30) [1-(Hydroxymethyl)-butyl]-pentadecanamide
(31) [1-(Hydroxymethyl)-butyl]-14-methylpentadecanamide
(32) [1-(Hydroxymethyl)-pentyl]-14-methylpentadecanamide
(33) [1-(Hydroxymethyl)-ethyl]-hexadecanamide
(34) [1-(Hydroxymethyl)-ethyl]-15-methylhexadecanamide
(35) [1-(Hydroxymethyl)-propyl]-15-methylhexadecanamide
(36) [1-(Hydroxymethyl)-pentyl]-15-methylhexadecanamide
(37) [1-(Hydroxymethyl)-ethyl]-heptadecanamide
(38) [1-(Hydroxymethyl)-pentyl]-heptadecanamide
(39) [1-(Hydroxymethyl)-propyl]-16-methylheptadecanamide
(40) [1-(Hydroxymethyl)-pentyl]-16-methylheptadecanamide
(41) [1-(Hydroxymethyl)-pentyl]-octadecanamide
(42) [1-(Hydroxymethyl)-butyl]-17-methyloctadecanamide
(43) [1-(Hydroxymethyl)-pentyl]-17-methyloctadecanamide
(44) [1-(Hydroxymethyl)-ethyl]-nonadecanamide
(45) [1-(Hydroxymethyl)-pentyl]-nonadecanamide
(46) [1-(Hydroxymethyl)-ethyl]-18-methylnonadecanamide
(47) [1-(Hydroxymethyl)-ethyl]-eicosanamide
(48) [1-(Hydroxymethyl)-butyl]-eicosanamide
(49) [1-(Hydroxymethyl)-butyl]-19-methyleicosanamide
(50) [1-(Hydroxymethyl)-ethyl]-heneicosanamide
(51) [1-(Hydroxymethyl)-propyl]-docosanamide
(52) [1-(Hydroxymethyl)-pentyl]-tricosanamide
(53) [1-(Hydroxymethyl)-pentyl]-tetracosanamide
(54) [1-(Hydroxymethyl)-butyl]-heptacosanamide
(55) [1-(Hydroxymethyl)-pentyl]-heptacosanamide
(56) [1-(Hydroxymethyl)-pentyl]-hexacosanamide
(57) [1-(Hydroxymethyl)-ethyl]-heptacosanamide
(58) [1-(Hydroxymethyl)-propyl]-octacosanamide
(59) [1-(Hydroxymethyl)-butyl]-triacontanamide
(60) [1-(Hydroxymethyl)-pentyl]-heptenamide
(61) [1-(Hydroxymethyl)-ethyl]-trans-9-hexadecenamide
(62) [1-(Hydroxymethyl)-propyl]-trans-9-hexadecenamide
(63) [1-(Hydroxymethyl)-pentyl]-trans-9-hexadecenamide
(64) [1-(Hydroxymethyl)-propyl]-(all-cis-11,14,17)-eicosatrienamide
(65) [1-(Hydroxymethyl)-butyl]-(all-cis-11,14,17)-eicosatrienamide
(66) [1-(Hydroxymethyl)-pentyl]-(all-cis-11,14,17)-eicosatrienamide
(67) [1-(Hydroxymethyl)-propyl]-cis-10-heptadecenamide
(68) [1-(Hydroxymethyl)-pentyl]-cis-10-heptadecenamide
(69) [1-(Hydroxymethyl)-pentyl]-cis-10-nonadecenamide
(70) [1-(Hydroxymethyl)-ethyl]-cis-3,cis-6-nonadienamide
(71) [1-(Hydroxymethyl)-butyl]-cis-3,cis-6-nonadienamide
(72) [1-(Hydroxymethyl)-ethyl]-cis-10-pentadecenamide
(73) [1-(Hydroxymethyl)-pentyl]-cis-10-pentadecenamide
(74) [1-(Hydroxymethyl)-butyl]-cis-12-octadecenamide
(75) [1-(Hydroxymethyl)-propyl]-cis-13-octadecenamide
(76) [1-(Hydroxymethyl)-pentyl]-cis-13-octadecenamide
(77) [1-(Hydroxymethyl)-ethyl]-cis-7-octadecenamide
(78) [1-(Hydroxymethyl)-ethyl]-cis-8-eicosenamide
(79) [1-(Hydroxymethyl)-butyl]-cis-8-eicosenamide
(80) [1-(Hydroxymethyl)-ethyl]-trans-9-tetradecenamide
(81) [1-(Hydroxymethyl)-propyl]-trans-9-tetradecenamide
(82) [1-(Hydroxymethyl)-pentyl]-trans-9-tetradecenamide
(83) [1-(Hydroxymethyl)-pentyl]-cis-9,cis-11-octadecadienamide
(84) [1-(Hydroxymethyl)-ethyl]-cis-9,cis-12-octadecadienamide
(85) [1-(Hydroxymethyl)-butyl]-cis-9,cis-12-octadecadienamide

(86) [1-(Hydroxymethyl)-propyl]-trans-9-octadecenamide
(87) [1-(Hydroxymethyl)-butyl]-trans-9-octadecenamide
(88) [1-(Hydroxymethyl)-ethyl]-cis-9-octadecenamide
(89) [1-(Hydroxymethyl)-propyl]-cis-9-octadecenamide
(90) [1-(Hydroxymethyl)-ethyl]-(all-trans-9,11,13,15)-octadecatetraenamide
(91) [1-(Hydroxymethyl)-pentyl]-(all-trans-9,11,13,15)-octadecatetraenamide
(92) [1-(Hydroxymethyl)-butyl]-(all-cis-9,11,13,15)-octadecatetraenamide
(93) [1-(Hydroxymethyl)-pentyl]-(all-cis-9,11,13,15)-octadecatetraenamide
(94) [1-(Hydroxymethyl)-ethyl]-cis-11-octadecenamide
(95) [1-(Hydroxymethyl)-pentyl]-cis-11-octadecenamide
(96) [1-(Hydroxymethyl)-ethyl]-cis-13-docosenamide
(97) [1-(Hydroxymethyl)-propyl]-(all-cis-13,16,19)-docosatrienamide
(98) [1-(Hydroxymethyl)-pentyl]-(all-cis-13,16,19)-docosatrienamide
(99) [1-(Hydroxymethyl)-ethyl]-(all-cis-9,12,15)-octadecatrienamide
(100) [1-(Hydroxymethyl)-ethyl]-(all-cis-8,11,14)-eicosatrienamide
(101) [1-(Hydroxymethyl)-propyl]-(all-cis-8,11,14)-eicosatrienamide
(102) [1-(Hydroxymethyl)-butyl]-(all-cis-8,11,14)-eicosatrienamide
(103) [1-(Hydroxymethyl)-pentyl]-(all-cis-8,11,14)-eicosatrienamide
(104) [1-(Hydroxymethyl)-ethyl]-trans-11-octadecenamide
(105) [1-(Hydroxymethyl)-pentyl]-trans-13-docosenamide
(106) [1-(Hydroxymethyl)-propyl]-trans-9,trans-12-octadecadienamide
(107) [1-(Hydroxymethyl)-ethyl]-cis-9-tetradecenamide
(108) [1-(Hydroxymethyl)-propyl]-cis-9-tetradecenamide
(109) [1-(Hydroxymethyl)-butyl]-cis-9-tetradecenamide
(110) [1-(Hydroxymethyl)-ethyl]-cis-9-hexadecenamide
(111) [1-(Hydroxymethyl)-methylbutyl]-cis-9-hexadecenamide
(112) [1-(Hydroxymethyl)-butyl]-cis-9-hexadecenamide
(113) [1-(Hydroxymethyl)-ethyl]-10-undecenamide
(114) [1-(Hydroxymethyl)-pentyl]-(all-cis-8,11,14)-eicosatrienamide
(115) [1-(Hydroxymethyl)-pentyl]-cis-11,cis-14-eicosadienamide
(116) [1-(Hydroxymethyl)-ethyl]-cis11-eicosenamide
(117) [1-(Hydroxymethyl)-pentyl]-cis-11-eicosenamide
(118) [1-(Hydroxymethyl)-ethyl]-cis-15-tetracosenamide
(119) [1-(Hydroxymethyl)-propyl]-cis-15-tetracosenamide
(120) [1-(Hydroxymethyl)-pentyl]-11-dodecenamide
(121) [1-(Hydroxymethyl)-ethyl]-9-decenamide
(122) [1-(Hydroxymethyl)-butyl]-16-heptadecenamide
(123) [1-(Hydroxymethyl)-ethyl]-(all-cis-11,14,17)-eicosatrienamide
(124) [1-(Hydroxymethyl)-butyl]-(all-cis-11,14,17)-eicosatrienamide
(125) [1-(Hydroxymethyl)-pentyl]-(all-cis-11,14,17)-eicosatrienamide
(126) [1-(Hydroxymethyl)-methylbutyl]-cis-13-eicosenamide
(127) [1-(Hydroxymethyl)-ethyl]-cis-13,cis-13-docosadienamide
(128) [1-(Hydroxymethyl)-propyl]-(all-cis-7,10,13,16)-docosatetraenamide
(129) [1-(Hydroxymethyl)-ethyl]-22-tricosenamide
(130) [1-(Hydroxymethyl)-ethyl]-9-tetradecynamide
(131) [1-(Hydroxymethyl)-butyl]-9-tetradecynamide
(132) [1-(Hydroxymethyl)-ethyl]-13-eicosynamide
(133) [1-(Hydroxymethyl)-ethyl]-10,12-nonacosadiinamide
(134) [1-(Hydroxymethyl)-ethyl]-10,12-octadecadiinamide
(135) [1-(Hydroxymethyl)-pentyl]-10,12-octadecadiinamide
(136) [1-(Hydroxymethyl)-butyl]-9-octadecynamide
(137) [1-(Hydroxymethyl)-propyl]-9-octadecynamide
(138) [1-(Hydroxymethyl)-methylbutyl]-9-octadecynamide
(139) [1-(Hydroxymethyl)-ethyl]-10-undecynamide
(140) [1-(Hydroxymethyl)-butyl]-10,12-tricosadiynamide
(141) [1-(Hydroxymethyl)-ethyl]-10,12-pentacosadiynamide
(142) [1-(Hydroxymethyl)-ethyl]-10,12-heptacosadiynamide The following examples exhibit some of the process variants that can be used to synthesize the compounds according to the invention. However, they are not intended to limit the subject matter of the invention. The structure of the compounds was ensured by $^1H$ and optionally by $^{13}C$-NMR spectroscopy. The purity of the substances was determined by means of C, H, N elemental analysis as well as by thin layer chromatography.

General Working Instructions

General Working Instruction A 25 mmol carboxylic acid of formula III is dissolved in 125 ml THF. After addition of 30 mmol 1,1'-carbonyldiimidazole it is boiled for 10 min under reflux. 50 mmol amino alcohol of formula II is added at room temperature. After a further 3 hours under reflux it is concentrated in a vacuum. The residue is taken up in diethyl ether, washed with water, 0.5 N NaOH and water. The organic phase is dried over magnesium sulfate and concentrated in a vacuum.

General Working Instruction B

A solution of 25 mmol chloroformic acid isobutyl ester dissolved in 25 ml absolute dichloromethane is added dropwise at −10° C. to a solution of 25 mmol carboxylic acid of formula III and 25 mmol triethylamine in 100 ml absolute dichloromethane. After 15 min a solution of 30 mmol amino alcohol of formula II and 30 mmol triethylamine in 75 ml absolute dichloromethane is added dropwise. It is stirred for a further 30 min at −10° C. before it is slowly heated to room temperature. The reaction mixture is concentrated in a vacuum, taken up in diethyl ether and washed with water, 0.5 N NaOH and water. The organic phase is dried over magnesium sulfate and concentrated in a vacuum.

General Working Instruction C

A solution of 25 mmol carboxylic acid chloride of formula III in 30 ml absolute dichloromethane is added dropwise at 10° C. to a solution of 25 mmol amino alcohol of formula II and 25 mmol triethylamine in 100 absolute dichloromethane. After stirring for 48 hours at room temperature it is concentrated in a vacuum, the residue is taken up in diethyl ether and washed with water, 0.5 N HCl and saturated NaCl. The organic phase is dried over magnesium sulfate and concentrated in a vacuum.

EXAMPLE 1

R-N-[1-(Hydroxymethyl)-propyl]-eicosanamide carboxylic acid: eicosanoic acid
alcohol: R-2-amino-1-butanol
It is prepared according to the general working instruction A. Yield 84% colourless crystals; Fp 90–92° C.

EXAMPLE 2

R-N-[1-(Hydroxymethyl)-propyl]-(all-cis-9, 12, 15)-octadecatrienamide carboxylic acid: linolenic acid
alcohol: R-2-amino-1-butanol
It is prepared according to the general working instruction B. It was purified by chromatography on silica gel with ethyl acetate/isohexane (1:1). Yield 61% colourless oil.

EXAMPLE 3

N-[1-(Hydroxymethyl)-pentyl]-eicosanamide carboxylic acid: eicosanoic acid
alcohol: 2-amino-1-hexanol
It is prepared according to the general working instruction C: yield 65% colourless crystals.

EXAMPLE 4

N-[1-(Hydroxymethyl)-pentyl]-cis-3,cis-6-nonadienamide carboxylic acid: cis-3,cis-6-nonadienoic acid
alcohol: 2-amino-1-hexanol
It is prepared according to the general working instruction B. It was purified by chromatography on silica gel with ethyl acetate/isohexane (1:1). Yield 35% colourless oil.

EXAMPLE 5

N-[1-(Hydroxymethyl)-pentyl]-nonanamide carboxylic acid: nonanoic acid
alcohol: 2-amino-1-hexanol
It is prepared according to the general working instruction A. Yield 95% colourless oil.

EXAMPLE 6

R-N-[1-(Hydroxymethyl)-3-methylbutyl]-(all-cis-9, 12, 15)-octadecatrienamide carboxylic acid: linolenic acid
alcohol: R-2-amino-4-methyl-1-pentanol
It is prepared according to the general working instruction B. It was purified by chromatography on silica gel with ethyl acetate/isohexane (1:1). Yield 94% colourless oil.

EXAMPLE 7

R-N-[1-(Hydroxymethyl)-butyl]-(all-cis-9, 12, 15)-octadecatrienamide carboxylic acid: linolenic acid
alcohol: R-2-amino-1-pentanol
It is prepared according to the general working instruction B. It was purified by chromatography on silica gel with ethyl acetate/isohexane (1:1). Yield 86% colourless oil.

EXAMPLE 8

R-N-[1-(Hydroxymethyl)-propyl]-cis-3,cis-6-nonadienamide carboxylic acid: cis-3,cis-6-nonadienoic acid
alcohol: R-2-amino-1-butanol Synthesis of cis-3,cis-6-nonadienoic acid cis-3,cis-6-Nonadien-1-ol (150 mmol) is dissolved in 140 ml acetone and admixed with a mixture of 14 g chromiumtrioxide in 42 ml water and 12.6 ml concentrated sulphuric acid. After 6 h at room temperature it is diluted with 70 ml water and the mixture is extracted with diethyl ether. The combined organic phases are extracted with soda solution, the soda solution is acidified and extracted with dichloromethane. After drying over magnesium sulfate it is concentrated and a colourless oil is obtained. (yield: 54%)
It is prepared according to the general working instruction A. Yield 95% colourless oil.

EXAMPLE 9

R-N-[1-Hydroxymethyl)-pentyl]-(all-cis-9, 12 15) octadecatrienamide carboxylic acid: linolenic acid
alcohol: R-2-amino-1-hexanol
It is prepared according to the general working instruction B. It was purified by chromatography on silica gel with ethyl acetate/isohexane (1:1). Yield 48% colourless oil.

EXAMPLE 10

R-N-[1-Hydroxymethyl)-pentyl]-cis-9,cis-12-octadecadienamide carboxylic acid: linoleic acid
alcohol: R-2-amino-1-hexanol
It is prepared according to the general working instruction C. It was purified by chromatography on silica gel with ethyl acetate/heptane (2:1). Yield 55% colourless oil.

EXAMPLE 11

N-[1-Hydroxymethyl)-pentyl]-cis-9-hexadecenamide carboxylic acid: palmitoleinic acid
alcohol: 2-amino-1-hexanol
It is prepared according to the general working instruction C. It was purified by chromatography on silica gel with ethyl acetate/heptane (1:1). Yield 75% colourless oil.

EXAMPLE 12

S-N-[1-Hydroxymethyl)-pentyl]-cis-9-octadecenamide carboxylic acid: oleic acid
alcohol: S-2-amino-1-hexanol
It is prepared according to the general working instruction C. It was purified by chromatography on silica gel with ethyl acetate/heptane (2:1). Yield 40% colourless amorphous powder.

EXAMPLE 13

S-N-[1-Hydroxymethyl)-pentyl]-9-octadecynamide carboxylic acid: octadecynoic acid
alcohol: S-2-amino-1-hexanol
It is prepared according to the general working instruction C. It was purified by chromatography on silica gel with ethyl acetate/heptane (2:1). Yield 51% colourless crystals.

EXAMPLE 14

R-N-[1-hydroxymethyl)-pentyl]-cis-9-octadecenamide carboxylic acid: oleic acid
alcohol: R-2-amino-1-hexanol
It is prepared according to the general working instruction C. It was purified by chromatography on silica gel with ethyl acetate/heptane (2:1). Yield 65% colourless crystals.

EXAMPLE 15

S-N-[1-Hydroxymethyl)-pentyl]-trans-9-octadecenamide carboxylic acid: elaidic acid
alcohol: S-2-amino-1-hexanol
It is prepared according to the general working instruction C. It was purified by chromatography on silica gel with ethyl acetate/heptane (2:1). Yield 55% colourless crystals.

EXAMPLE 16

R-N-[1-Hydroxymethyl)-pentyl]-9-octadecynamide carboxylic acid: octadecynoic acid
alcohol: R-2-amino-1-hexanol
It is prepared according to the general working instruction C. It was purified by chromatography on silica gel with ethyl acetate/heptane (2:1). Yield 61% colourless crystals.

EXAMPLE 17

R-N-[1-Hydroxymethyl)-pentyl]-trans-9-octadecenamide carboxylic acid: elaidic acid
alcohol: R-2-amino-1-hexanol
It is prepared according to the general working instruction C. It was purified by chromatography on silica gel with ethyl acetate/heptane (2:1). Yield 54% colourless amorphous powder.

EXAMPLE 18

R-N-[1-Hydroxymethyl)-pentyl]-eicosanamide carboxylic acid: eicosanoic acid
alcohol: R-2-amino-1-hexanol
It is prepared according to the general working instruction C. It was purified by chromatography on silica gel with ethyl acetate/heptane (2:1). Yield 49% colourless crystals.

EXAMPLE 19

N-[1-Hydroxymethyl)-pentyl]-cis-9-tetradecenamide carboxylic acid: myristeoleic acid
alcohol: 2-amino-1-hexanol
It is prepared according to the general working instruction C. It was purified by chromatography on silica gel with ethyl acetate/heptane (2:1). Yield 84% colourless oil.

EXAMPLE 20

N-[1-Hydroxymethyl)-pentyl]-9-octadecynamide carboxylic acid: octadecynoic acid
alcohol: 2-amino-1-hexanol
It is prepared according to the general working instruction C. It was purified by chromatography on silica gel with ethyl acetate/heptane (1:1). Yield 65% colourless oil.

EXAMPLE 21

N-[1-Hydroxymethyl)-pentyl]-trans-9-octadecenamide carboxylic acid: elaidic acid
alcohol: 2-amino-1-hexanol
It is prepared according to the general working instruction C. It was purified by chromatography on silica gel with ethyl acetate/heptane (1:1). Yield 80% colourless oil.

EXAMPLE 22

N-[1-Hydroxymethyl)-pentyl]-9-tetradecynamide carboxylic acid: tetradecynoic acid
alcohol: 2-amino-1-hexanol
It is prepared according to the general working instruction C. It was purified by chromatography on silica gel with ethyl acetate/heptane (2:1). Yield 92% colourless oil.

EXAMPLE 23

S-N-[1-Hydroxymethyl)-pentyl]-cis-9,cis-12-octadecadienamide carboxylic acid: linoleic acid
alcohol: 2-amino-1-hexanol
It is prepared according to the general working instruction C. It was purified by chromatography on silica gel with ethyl acetate/heptane (2:1). Yield 47% colourless oil.

EXAMPLE 24

N-[1-Hydroxymethyl)-pentyl]-cis-9,cis-12-octadecadienamide carboxylic acid: linoleic acid
alcohol: 2-amino-1-hexanol
It was prepared according to the general working instruction B. Yield 98% colourless oil.

EXAMPLE 25

N-[1-Hydroxymethyl)-pentyl]-6-heptenamide carboxylic acid: 6-heptenoic acid
alcohol: 2-amino-1-hexanol
It was prepared according to the general working instruction B. Yield 92% colourless oil.

EXAMPLE 26

N-[1-Hydroxymethyl)-pentyl]-cis-9-octadecenamide carboxylic acid: oleic acid
alcohol: 2-amino-1-hexanol
It was prepared according to the general working instruction A. Yield 78% colourless oil.

EXAMPLE 27

R-N-[1-Hydroxymethyl)-propyl]-cis-9,cis-12-octadecadienamide carboxylic acid: linoleic acid
alcohol: R-2-amino-1-butanol
It was prepared according to the general working instruction B. It was purified by chromatography on silica gel with ethyl acetate. Yield 54% colourless oil.

EXAMPLE 28

S-N-[1-Hydroxymethyl)-propyl]-cis-9,cis-12-octadecadienamide carboxylic acid: linoleic acid
alcohol: S-2-amino-1-butanol
It was prepared according to the general working instruction B. It was purified by chromatography on silica gel with ethyl acetate. Yield 48% colourless oil.

EXAMPLE 29

N-[1-Hydroxymethyl)-ethyl]-trans-9-octadecenamide carboxylic acid: elaidic acid
alcohol: 2-amino-1-propanol It was prepared according to the general working instruction B. It was purified by chromatography on silica gel with ethyl acetate. Yield 72% colourless oil.

EXAMPLE 30

N-[1-Hydroxymethyl)-butyl]-cis-9-octadecenamide carboxylic acid: oleic acid
alcohol: 2-amino-1-pentanol It is prepared according to the general working instruction C. It was purified by chromatography on silica gel with ethyl acetate/heptane (3:1). Yield 88% colourless oil.

EXAMPLE 31

N-[1-Hydroxymethyl)-ethyl]-9-octadecynamide carboxylic acid: octadecynoic acid
alcohol: 2-amino-1-propanol It is prepared according to the general working instruction C. It was purified by chromatography on silica gel with ethyl acetate/heptane (1:1). Yield 68% colourless oil.

EXAMPLE 32

Compounds of formula (I) were examined in a DNA synthesis assay in primary cultures of osteoblasts from fetal rat calvariae. The experiments were carried out in accordance with Pfeilschifter et al., Endocrinology 126, 703 (1990).

Primary osteoblasts were isolated from foetal rat calvariae by sequential digestion with collagenase. In this process 5 cell fractions were obtained. A pool from the cell fractions 3–5 were cultured in vitro. The cells were cultured in an incubator at a relative air humidity of 95%, a $CO_2$ content of 5% and a temperature of 37° C. The test substances were examined in the cultures of the first, second or third cell passage. For the examinations the cells were sown at a cell count of $7 \times 10^3$ cells (in 100 µl culture medium)/well in microtitre plates at least 76 hours before applying the test substances. MEM Dulbecco (plus 4.5 g/l glucose plus 3.7 g/l $NaHCO_3$ without glutamine) was used as the culture medium to which 5% foetal calf serum (FCS) and 5000 U/ml penicillin/streptomycin had been added. Immediately before addition of the test substances to the cell culture the medium was replaced by 150 µl medium which contained 1 mg/ml bovine serum albumin (BSA) instead of FCS. Test substances were added at the desired concentrations to the medium containing BSA. $TGF\beta_1$ (transforming growth factor $\beta_1$) at concentrations of 0.1–0.2 ng/ml were also examined as a positive control. Three determinations were carried out per (positive) control or substance concentration. The cell cultures were incubated for 24 hours with test substances, a thymidine probe (1 µCi methyl-$^3$H-thymidine in 20 µl PBS solution) being additionally present during the last 3 hours. At the end of the incubation period the cell cultures were washed three times with 0.9% saline solution and subsequently admixed with 100 µl liquid scintillator each time (OptiPhase Supermix TM®). Afterwards the radioactivity incorporated into the DNA was measured in cpm in a liquid scintillation counter (1450 MicroBeta®). Cell cultures which had only received medium containing BSA served as controls (100%).

TABLE I

Rate of DNA synthesis of primary osteoblastic cells of foetal rat calvariae in percent compared to the control (=100%)

| Compound | Example | 1 µg/ml |
|---|---|---|
| N-[1-hydroxymethyl)-pentyl]-(all-cis-9,12,15)-octadecatrienamide | 9 | 367 |
| N-[1-hydroxymethyl)-pentyl]-cis-9,cis-12-octadecadienamide | 10 | 475 |
| N-[1-hydroxymethyl)-pentyl]-cis-9-hexadecenamide | 11 | 191 |
| N-[1-hydroxymethyl)-pentyl]-cis-9-tetradecenamide | 19 | 298 |
| N-[1-hydroxymethyl)-pentyl]-9-octadecynamide | 20 | 250 |
| N-[1-hydroxymethyl)-pentyl]-trans-9-octadecenamide | 21 | 188 |
| N-[1-hydroxymethyl)-pentyl]-cis-9,cis-12-octadecadienamide | 24 | 223 |
| N-[1-hydroxymethyl)-pentyl]-cis-9-octadecenamide | 26 | 296 |
| N-[1-hydroxymethyl)-propyl]-cis-9,cis-12-octadecadienamide | 27 | 252 |

What is claimed is:
1. A process for the production of compounds of formula I

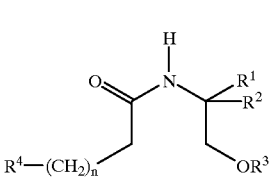

(I)

in which

R$^1$ denotes hydrogen or methyl

R$^2$ denotes lower straight-chained or branched alkyl with 1 to 10 carbon atoms, provided that when R$^2$ denotes methyl or isobutyl, —(CH$_2$)$_n$—R$^4$ is not (all-cis-4,7,10,13)-octadecatetraenyl or an unbranched chain with 14 carbon atoms R$^3$ denotes hydrogen or lower alkyl n denotes 0–12

R$^4$ denotes alkyl, alkenyl or alkinyl with 6 to 24 carbon atoms, provided that when R$^4$ denotes alkyl, —(CH$_2$)$_n$—R$^4$ is not an unbranched alkyl chain with 8, 10, 12, 14 or 16 carbon atoms as well as pharmacologically acceptable salts and optical isomers thereof; said process comprising reacting a compound of formula II

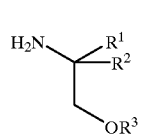

(II)

in which R$^1$, R$^2$, and R$^3$ have the above meanings either with (a) a compound of formula III

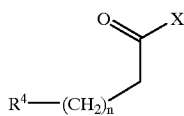

(III)

in which $R^4$ and n have the above meanings and X represents an activating group or (b) with a compound of formula IV $R^4$—$(CH_2)_{n+1}$—CN (IV) in which $R^4$ and n have the above meanings.

2. The process of claim 1, wherein the compounds obtained are converted into other compounds of formula I.

3. The process of claim 1, wherein the compounds obtained are converted into pharmacologically acceptable salts.

4. The process of claim 1, wherein the compounds obtained are converted into optical isomers.

5. Compounds of formula I

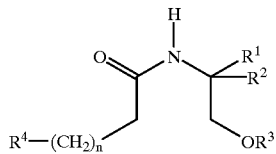

(I)

in which $R^1$=hydrogen or methyl $R^2$=lower straight-chained or branched alkyl with 1 to 10 carbon atoms, with the proviso that when $R^2$ is isopropyl, then —$(CH_2)_n$—$R^4$ may not be an unbranched chain with 6 or 10 carbon atoms, when $R^2$ is methyl, then $R^1$ is hydrogen, and $(CH_2)_4$—$R^4$ may not be (all-cis-3, 6, 9, 12)-octadecatetranenyl, (all-cis-4,7,10,13)-octadecatetraene or an unbranched chain with 14 carbon atoms, and when $R^2$ is isobutyl, then $(CH_2)_4$—$R^4$ may not be (all-cis-4,7,10,13)-octadecatetraene, $R^3$=hydrogen n=0–12

$R^4$=alkyl, alkenyl or alkinyl with 6 to 24 carbon atoms, with the proviso that when $R^4$ is alkyl, —$(CH_2)_4$—$R^4$ may not be an unbranched alkyl chain with 6, 8, 10, 12 14 or 16 carbon atoms, as well as pharmacologically acceptable salts and optical isomers thereof.

6. A pharmaceutical compostion containing at least one compound of formula I

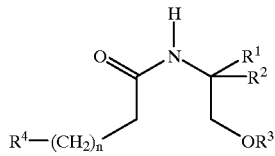

(I)

in which $R^1$ denotes hydrogen or methyl $R^2$ denotes lower straight-chained or branched alkyl with 1 to 10 carbon atoms, with the proviso that when $R^2$ is isopropyl, then —$(CH_2)_n$—$R^4$ may not be an unbranched chain with 6 or 10 carbon atoms, and when $R^2$ is methyl, then $R^1$ is hydrogen, and —$(CH_2)_4$—$R^4$ may not be (all-cis-3, 6, 9, 12)-octadecatetranenyl, or an unbranched chain with 14 carbon atoms $R^3$ denotes hydrogen [or lower alkyl]

n denotes 0–12

$R^4$ denotes alkyl, alkenyl or alkinty with 6 to 24 carbon atoms, which the proviso that when $R^4$ is alkyl, then —$(CH_2)_4$—$R^4$ may not be an unbranched alkyl chain with 6, 8, 10, 12 14 or 16 carbon atoms, in addition to common carrier and auxiliary substances.

7. A method for treating osteoporosis in a patient in need of such treatment, comprising administering to said patient a therapeutically effective amount of a composition of claim 6.

8. A method for treating osteoporosis in a patient in need of such treatment, comprising administering to said patient, a therapeutically effective amount of a compound of claim 5.

\* \* \* \* \*